US012665073B1

(12) United States Patent
Sinha et al.

(10) Patent No.: US 12,665,073 B1
(45) Date of Patent: Jun. 23, 2026

(54) AI-DRIVEN SYSTEM AND METHODS FOR 3D MEDICAL IMAGE DISEASE DETECTION

(71) Applicant: Cornerstone Eagle LLC, Desoto, TX (US)

(72) Inventors: Aviraj Sinha, Dallas, TX (US); Sajed M. Khan, Prosper, TX (US); Lucas L. Stamatis, Mineola, TX (US)

(73) Assignee: Cornerstone Eagle LLC, Desoto, TX (US)

( * ) Notice: Subject to any disclaimer, the term of this patent is extended or adjusted under 35 U.S.C. 154(b) by 0 days.

(21) Appl. No.: 19/200,539

(22) Filed: May 6, 2025

(51) Int. Cl.
| | |
|---|---|
| *G16H 30/40* | (2018.01) |
| *G06T 7/00* | (2017.01) |
| *G06T 7/155* | (2017.01) |
| *G06T 7/174* | (2017.01) |

(52) U.S. Cl.
CPC ........... *G16H 30/40* (2018.01); *G06T 7/0016* (2013.01); *G06T 7/155* (2017.01); *G06T 7/174* (2017.01); *G06T 2207/10028* (2013.01); *G06T 2207/20081* (2013.01); *G06T 2207/20224* (2013.01)

(58) Field of Classification Search
CPC . G06T 2207/20081; G06T 2207/20084; G06T 7/0012; G06T 7/143; G06T 2207/20076; G06T 5/50; G06T 17/00; G06T 7/174; G06T 7/155; G06T 7/0016; G06T 2207/10028; G06T 2207/20224; G06V 2201/03; A61B 5/7264; G16H 30/40; G16H 50/20; G16H 30/20; G16H 30/00
See application file for complete search history.

(56) References Cited

U.S. PATENT DOCUMENTS

| | | | | |
|---|---|---|---|---|
| 9,754,371 | B2 * | 9/2017 | Kateb | .................. A61B 5/0042 |
| 11,756,675 | B2 | 9/2023 | Orringer et al. | |
| 2020/0167928 | A1 * | 5/2020 | Heindl | .................. A61B 5/055 |
| 2024/0378724 | A1 | 11/2024 | Park et al. | |

* cited by examiner

*Primary Examiner* — Courtney Joan Nelson
(74) *Attorney, Agent, or Firm* — Alix, Yale & Ristas, LLP

(57) ABSTRACT

The disclosure provides a unified system and method for analyzing 3D medical images through probabilistic masking, multimodal embedding generation, anomaly detection, and reinforcement learning-based refinement. The methods comprise applying ailment-aware probabilistic masking to 3D medical scans using prior distributions of known abnormalities to retain diagnostically relevant voxel regions. The masked scans are encoded into latent vectors using a vision transformer encoder, while associated textual medical reports are encoded using a language model; both are mapped into a shared embedding space. Anomaly detection is performed through (1) a temporal comparison method based on differences in patient embeddings across time, and (2) a similarity-based method comparing current embeddings to a database of known abnormal cases using cosine similarity. Reinforcement learning is applied to refine embeddings using human expert feedback, including corrected annotations and textual clarifications, allowing dynamic adjustment of thresholds and encoder parameters. This adaptive framework supports efficient, scalable, and accurate medical diagnosis across a variety of imaging modalities.

12 Claims, 3 Drawing Sheets

AI-DRIVEN SYSTEM AND METHODS FOR 3D MEDICAL IMAGE DISEASE DETECTION

TECHNICAL FIELD

The present disclosure relates to the field of medical imaging and machine learning. More specifically, the disclosure pertains to systems and methods for processing and analyzing three-dimensional (3D) medical images using artificial intelligence techniques to generate lower-dimensional vector representations for clinical analysis and anomaly detection.

BACKGROUND

Medical imaging, particularly MRI and CT scans, plays a pivotal role in diagnosing and managing a wide range of medical conditions across nearly all areas of medicine. However, traditional methods for interpreting these scans face significant challenges, including a high dependence on radiologists, leading to variability in interpretations and potential delays. Additionally, these methods rely heavily on manual feature extraction and annotation, which are time-consuming and require extensive expert input. Another limitation is the difficulty in analyzing longitudinal data effectively, making it challenging to track subtle disease progression over time.

While machine learning has been introduced to assist in analyzing CT and MRI scans, most current efforts are based on supervised learning techniques that require manually labeled datasets. A major limitation of these methods is their inability to identify rare diseases, as labeled datasets tend to be biased toward more common conditions, leaving rare or new diseases underrepresented and often undetectable by these models. These approaches, as a result, demand substantial human intervention, making them labor-intensive and prone to bias and inconsistency. More recently, Retrieval-Augmented Generation (RAG) systems have demonstrated success in encoding and retrieving textual information in a compressed numerical format, allowing for efficient search through embeddings to find related text without manual labeling. Although these advancements have proven effective in natural language processing, applying them to medical imaging—a fundamentally different domain that uses 3D spatial information—remains underdeveloped, with most AI models still focused on textual feature extraction. We note that to create the model that encodes embeddings from 3D medical images requires certain storage and computer resources.

Despite the progress in AI-driven retrieval, there has yet to be a method for searching through 3D medical images using embeddings. Current techniques lack the ability to extract and utilize latent characteristics that could enable disease detection without requiring predefined labels.

SUMMARY

The disclosed methods and system address this gap by extending RAG principles to 3D medical imaging through supporting technologies, allowing vast amounts of imaging data to be used for detecting diseases that may not have been previously identified. Rather than relying on manually obtained features and labels, this approach focuses on discovering inherent patterns within the medical images, providing a more scalable and efficient method for diagnosis.

To achieve this, an AI-driven framework is introduced that generates structured 1D embeddings from 3D scans for medical imaging through the application of ailment-aware probabilistic masking. A prior probability distribution is computed by aggregating voxel intensities across historical datasets, and a spatial mask is generated by thresholding this distribution, selectively retaining voxels with higher likelihoods of containing pathological features. This masking step functions as a three-dimensional attention mechanism, ensuring that embedding generation focuses on clinically relevant regions and minimizes computational overhead.

Masked 3D scans are encoded into embedding vectors using a vision transformer-based encoder, while associated textual medical reports are encoded into corresponding vectors using a language model-based encoder. Both embeddings are projected into a shared latent space using modality-specific projection weights and combined via weighted summation, producing multimodal embeddings that are stored in a vector database for downstream comparison and retrieval. This design enables robust multimodal understanding of patient data across imaging and textual sources.

The system employs two complementary anomaly detection methods. First, temporal anomaly detection computes the difference between patient embeddings across timepoints, calculating the norm of the difference vector. The system dynamically determines an anomaly threshold by computing a running mean and standard deviation of historical embedding shifts, modulated by a tunable sensitivity parameter, ensuring adaptive and individualized anomaly detection. Second, similarity-based anomaly detection compares the new scan embedding against a database of embeddings representing known anomalies using cosine similarity, identifying anomalies based on divergence from known pathological cases.

To further enhance robustness and adaptability, a custom embedding threshold is introduced to account for natural variations in imaging data, preventing false positives while maintaining high sensitivity for meaningful anomalies. Embedding-based anomaly detection requires significantly fewer floating-point operations than traditional neural networks, allowing for highly efficient, scalable deployment across clinical systems.

An advancement of the disclosed methods is the integration of human-in-the-loop reinforcement learning for continuous improvement. Radiologists provide feedback via segmentation masks and textual annotations. The system computes reward signals based on overlap between predicted and corrected segmentations (using measures like Dice coefficient or Intersection over Union) and based on semantic similarity between predicted and corrected textual reports (using TF-IDF weighted cosine similarity). These rewards are used to refine encoder parameters and/or update latent vector representations through reinforcement learning update rules, incrementally improving the model without requiring full retraining.

The disclosed methods provide an advanced AI-driven framework that enables automated disease detection and anomaly identification across a wide range of medical conditions. By leveraging probabilistic masking and 3D embedding search, the disclosed system enhances diagnostic accuracy and facilitates early detection of abnormalities that may otherwise go unnoticed. The following are areas where the disclosed methods have demonstrated significant applicability:

Neurological Conditions: Brain tumors, strokes, multiple sclerosis, epilepsy, Alzheimer's disease, and more.

Cardiovascular Conditions: Coronary artery disease, cardiomyopathy, aortic aneurysms, and pulmonary embolisms.

Musculoskeletal Disorders: Bone fractures, joint dislocations, osteoarthritis, and scoliosis.

Pulmonary Diseases: Lung cancer, pneumonia, COPD, and pulmonary fibrosis.

Abdominal and Pelvic Conditions: Liver diseases, kidney stones, appendicitis, and uterine conditions.

Endocrine and Metabolic Disorders: Thyroid and adrenal gland disorders, diabetes complications, and pituitary abnormalities.

MRI, CT scans, and other 3D medical images are indispensable tools for detecting cancers, infections, spinal disorders, and traumatic injuries. However, traditional diagnostic methods rely heavily on manual interpretation, making them prone to variability and limited in their ability to identify rare or emerging diseases. Objects of the disclosure are to improve upon existing systems by employing AI-powered anomaly detection and adaptive learning frameworks, allowing for more precise, scalable, and data-driven medical imaging analysis.

The disclosure provides a system and methods for automated analysis of three-dimensional (3D) medical images using a combination of probabilistic masking, latent vector embedding, anomaly detection, and reinforcement learning updates. The methods generate contextually rich, low-dimensional embeddings from both imaging data and textual reports, facilitating unsupervised and semi-supervised medical anomaly detection.

The disclosed methods begin by applying ailment-aware masking to 3D medical scans using prior distributions computed from historical data. This masking step selectively retains voxel regions that are statistically more likely to contain pathological abnormalities, thereby reducing data dimensionality and focusing downstream processing on diagnostically relevant areas.

Masked 3D scans are processed through a neural encoder to produce latent embeddings, which are stored in a vector database. Associated textual medical reports are encoded into the same latent space using a language model. These multimodal embeddings support downstream tasks such as anomaly detection through temporal comparison of embeddings across time points or similarity-based comparison against a database of known anomalies using cosine similarity.

In some embodiments, the embedding space is further refined using expert feedback through a reinforcement learning framework. Radiologists provide feedback in the form of corrected segmentation masks or textual annotations, which are translated into reward signals for updating the encoder or latent vectors. This human-in-the-loop mechanism enables continuous embedding improvement without full retraining of the embedding encoder.

By combining unsupervised learning, probabilistic masking, and expert feedback, embodiments of the disclosed system enable scalable and adaptive detection of anomalies in 3D medical imaging without requiring fully labeled datasets. This approach allows for generalization across a broad range of medical conditions while maintaining computational efficiency and clinical interpretability.

OBJECTS OF THE DISCLOSURE

It is an object of this disclosure to provide an AI-powered masking model that efficiently processes 3D medical images by applying probabilistic mapping. This masking method enhances diagnostic accuracy by isolating relevant anatomical structures while reducing computational overhead, ensuring that medical imaging analysis is both efficient and precise.

Another object of the disclosure is to introduce an advanced encoding mechanism that converts 3D medical images into latent vector representations while simultaneously incorporating textual medical reports into the same embedding space. This embedding process takes in the masked data and further focuses on important features such as edge information. This unified representation facilitates improved retrieval, comparison, and contextual understanding of medical data.

A further object of the disclosure is to develop a specialized vector-based query and search mechanism to minimize false positives caused by variations in latent vector distributions. The primary anomaly detection method relies on time differential analysis, which tracks changes in a patient's latent vector representation over time to detect significant medical variations. Additionally, a secondary anomaly detection approach is based on cosine similarity, where new embeddings are compared against a database of known anomalies. The time-differential method operates in a fully unsupervised manner, while the similarity-based approach is semi-supervised, leveraging an existing set of labeled anomalies to establish detection thresholds.

It is also an object of this disclosure to introduce an adaptive anomaly detection framework that integrates human-in-the-loop feedback. While the system initially operates in a fully automated manner, expert validation can be incorporated to refine detection thresholds, adjust similarity metrics, and enhance the long-term performance of the embeddings for anomaly detection. This ensures continuous improvement and adaptability to evolving medical datasets.

A final object of the disclosure is to provide an efficient, scalable, and interpretable AI-driven framework for medical imaging that supports automated segmentation, anomaly detection, and retrieval-based diagnostics. By leveraging latent vector representations and adaptive learning mechanisms, embodiments of the disclosed system enable a robust and generalizable approach to medical anomaly detection, reducing dependence on extensive labeled datasets and improving early disease detection.

Definitions and Terminology

Medical Imaging—The process of creating visual representations of the interior of a body for clinical analysis and medical intervention. Examples include, but are not limited to MRI, CT scans, and X-rays. Medical imaging is used for diagnosis, treatment planning, and monitoring of diseases.

MRI (Magnetic Resonance Imaging)—A non-invasive imaging technology that produces detailed 3D images of organs and tissues using strong magnetic fields and radio waves, commonly used for neurological, musculoskeletal, and cardiovascular assessments.

CT Scan (Computed Tomography)—A medical imaging technique that uses X-ray measurements taken from different angles to create cross-sectional images of the body, often used for detecting fractures, tumors, and vascular diseases.

Voxel (Volumetric Pixel)—The 3D equivalent of a pixel in 2D images, representing a discrete unit of volume in a three-dimensional space. Voxels are fundamental in medical imaging as they define the resolution and detail of scans.

Embeddings—High-dimensional feature vectors that encode statistical information about data, such as text or images, into a lower-dimensional numerical representation that preserves semantic relationships. In the context of medical imaging, embeddings are used to capture and compare structural and pathological patterns in 3D scans.

Unsupervised Learning—A machine learning approach where models identify patterns in unlabeled data by clustering similar samples, learning latent structures, or generating pseudo-labels internally. This technique is critical for anomaly detection in medical imaging where labeled data is scarce.

Semi-Supervised Learning—A hybrid machine learning approach that combines a small set of labeled data with a larger set of unlabeled data to improve model performance. In this invention, semi-supervised learning facilitates anomaly detection by leveraging a set of known labeled anomalies while learning from the intrinsic structure of medical data to classify unknown cases.

Supervised Learning—A learning paradigm in which models are trained on labeled datasets with predefined disease classifications. Traditional AI models in medical imaging rely heavily on supervised learning, which limits adaptability to new or rare diseases and often requires large, manually labeled datasets, making them computationally expensive and impractical in real-world clinical settings.

Transformer Model—A deep learning architecture primarily designed for sequence-based tasks, using self-attention mechanisms to capture contextual relationships. Transformers are widely used in NLP but have emerging applications in medical imaging for feature extraction and anomaly detection.

BERT (Bidirectional Encoder Representations from Transformers)—A transformer model trained for natural language processing (NLP) tasks that learns contextual embeddings by predicting missing words in a sentence. While primarily designed for text, BERT-like architectures have applications in medical data analysis.

CLIP (Contrastive Language-Image Pretraining)—A deep learning model to align text and image representations in a shared embedding space, enabling cross-modal retrieval. This concept relates to aspects of the disclosed methods for encoding medical images in a searchable numerical format.

Cosine Similarity—A mathematical metric that measures the similarity between two vectors by computing the cosine of the angle between them. In this disclosure, cosine similarity is used for comparing medical embeddings to detect anomalies.

Dimensionality Reduction—The process of reducing the number of features in data while retaining its essential characteristics, often achieved using methods like Principal Component Analysis (PCA) or autoencoders. In medical imaging, dimensionality reduction helps convert high-dimensional scan data into compact embeddings.

Vision Transformer (VIT)—A deep learning architecture that applies transformer models, originally developed for natural language processing, to image data by dividing images into patches and processing them as sequences. ViTs enable efficient learning of spatial relationships and global context in visual data, making them highly effective for tasks like image classification and segmentation in medical imaging.

Sobel Edge Detection—A classical image processing technique that uses convolutional filters to detect edges by calculating the gradient magnitude of pixel intensity in horizontal and vertical directions. Sobel edge detection is commonly used in preprocessing pipelines to highlight anatomical boundaries and structural changes in medical scans.

Masking—A technique in machine learning where certain parts of the input data are hidden or ignored during training or inference. In computer vision and medical imaging, masking is often used to focus the model's attention on regions of interest or to exclude irrelevant or noisy data. In transformer models, masking helps control the flow of information, such as preventing future tokens from being seen in sequence prediction tasks.

Segmentation—A process in computer vision and medical imaging that involves partitioning an image into distinct regions or segments based on features such as intensity, texture, or shape. In medical applications, segmentation is used to isolate anatomical structures or pathological regions (e.g., tumors, organs) from surrounding tissue, enabling precise analysis, measurement, and diagnosis.

Anomaly Detection—The identification of patterns in data that deviate from expected behavior, commonly used in medical imaging to detect abnormalities such as tumors, lesions, or degenerative conditions.

Retrieval-Augmented Generation (RAG)—A machine learning approach where a system retrieves relevant data from an external database to enhance the accuracy of a generative model. This invention extends RAG principles to medical imaging, allowing structured search and retrieval of 3D medical scans.

Latent Space—A lower-dimensional space where compressed representations of data (e.g., medical images) are stored. In Variational Autoencoders (VAEs), latent space is structured so that similar images have similar latent representations, allowing for efficient anomaly detection.

Embedding Vector—A numerical representation of data in a lower-dimensional space that captures essential features while reducing complexity. Unlike latent vectors in VAEs, which follow probabilistic distributions, embedding vectors in this invention are deterministic representations optimized for medical image retrieval and anomaly detection.

Reinforcement Learning—A type of machine learning where an agent learns to make decisions by interacting with an environment and receiving feedback in the form of rewards or penalties. The agent's goal is to learn a policy that maximizes cumulative reward over time, making reinforcement learning well-suited for tasks involving sequential decision-making and control.

Rewards—Scalar feedback signals provided to an agent in reinforcement learning to evaluate the quality of its actions. Rewards guide the learning process by reinforcing behaviors that lead to desirable outcomes and discouraging those that do not, thereby shaping the agent's policy over time.

TF-IDF (Term Frequency-Inverse Document Frequency)—A statistical measure used in natural language processing to evaluate how important a word is to a document relative to a collection of documents. It combines the frequency of a term in a document (TF) with the inverse frequency of that term across all documents (IDF), allowing for more meaningful keyword extraction by down-weighting common terms and emphasizing rare but informative ones.

Bayesian Inference—A statistical method that updates the probability estimate for a hypothesis as more evidence or information becomes available. It relies on Bayes' Theorem to combine prior knowledge with new data, allowing for probabilistic reasoning under uncertainty.

DETAILED DESCRIPTION

Figure 1:
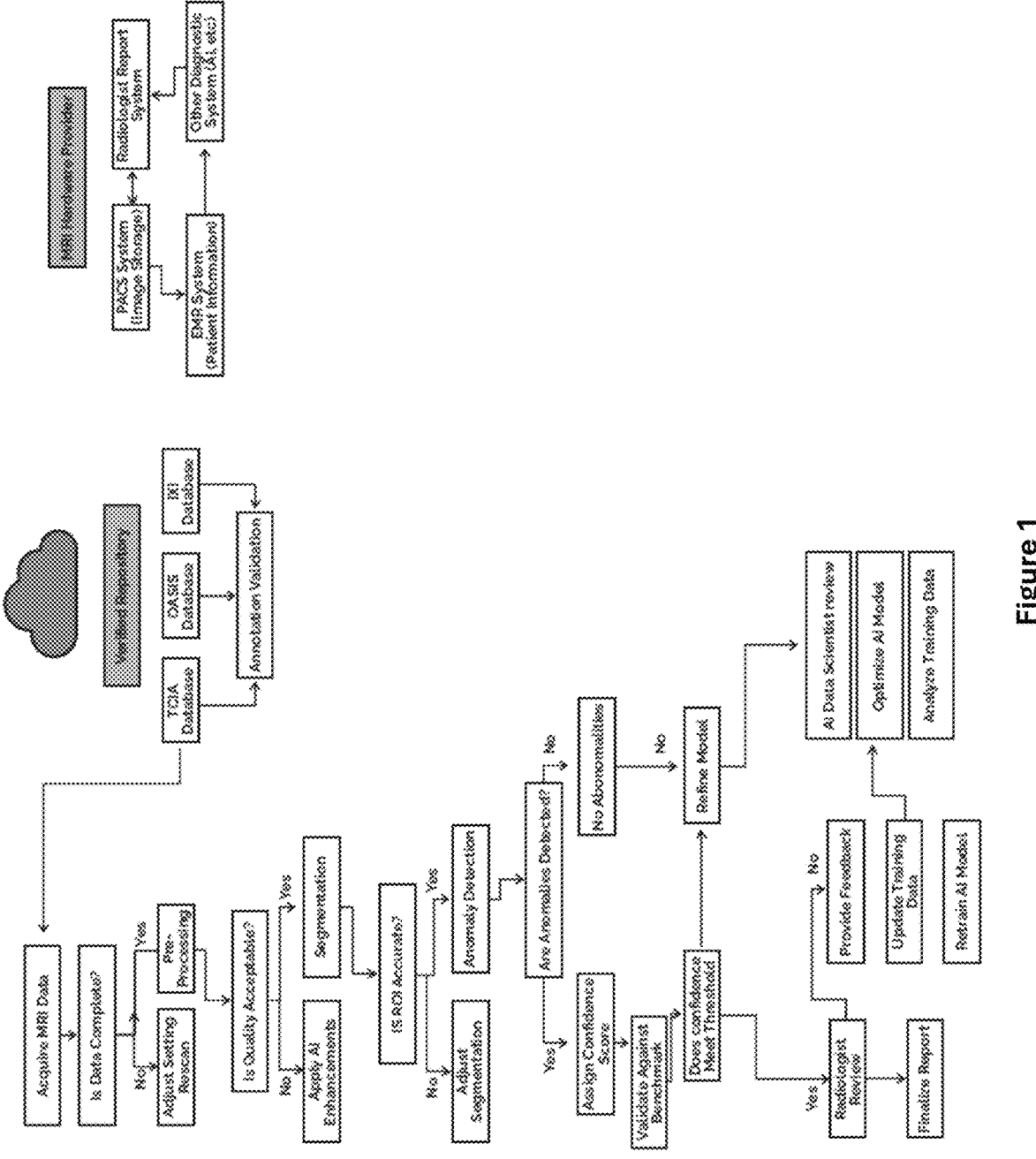
FIG. 1 is a flow chart illustrating the disclosed method and block diagrams illustrating embodiments of a system on which the method will be operate.

FIG. 1 outlines a disclosed process for acquiring and preparing medical image data before segmentation. It begins with sourcing MRI scans (or other medical images) from medical imaging databases (e.g., TCIA, OASIS, IXI) and conducting a completeness check. If data is missing, a rescan is performed. Preprocessing ensures data quality, with AI-based enhancements applied if necessary. Once validated, the high-quality medical image data is stored in a repository, ensuring consistency and reliability before segmentation.

Figure 2:
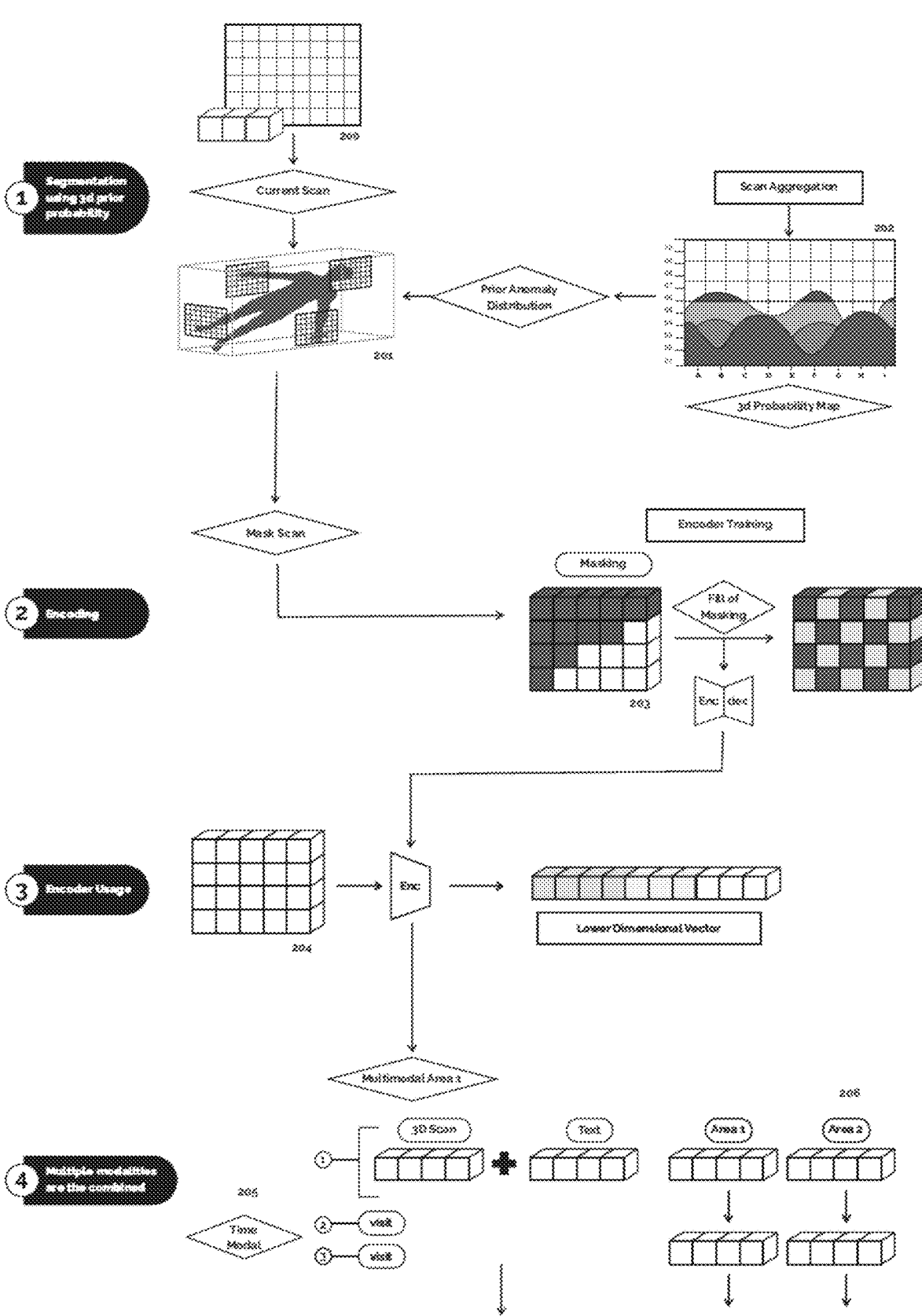
FIG. 2 illustrates four steps in one embodiment of a disclosed method according to aspects of the disclosure.

FIG. 2 summarizes a disclosed process for using machine learning embeddings for medical anomaly detection. FIG. 2 illustrates multiple steps: obtaining and aligning MRI images, generating probability maps, segmenting relevant regions, and encoding the information into lower-dimensional embeddings. According to aspects of the disclosure, these embeddings can be used for detecting anomalies across multiple patient visits (time-based comparison) or by comparing with known anomalies using similarity metrics. The framework also integrates textual embeddings with image data for improved contextual understanding, and radiologist feedback is incorporated to refine embeddings without retraining the entire model for the generation of a new embedding.

Figure 3:
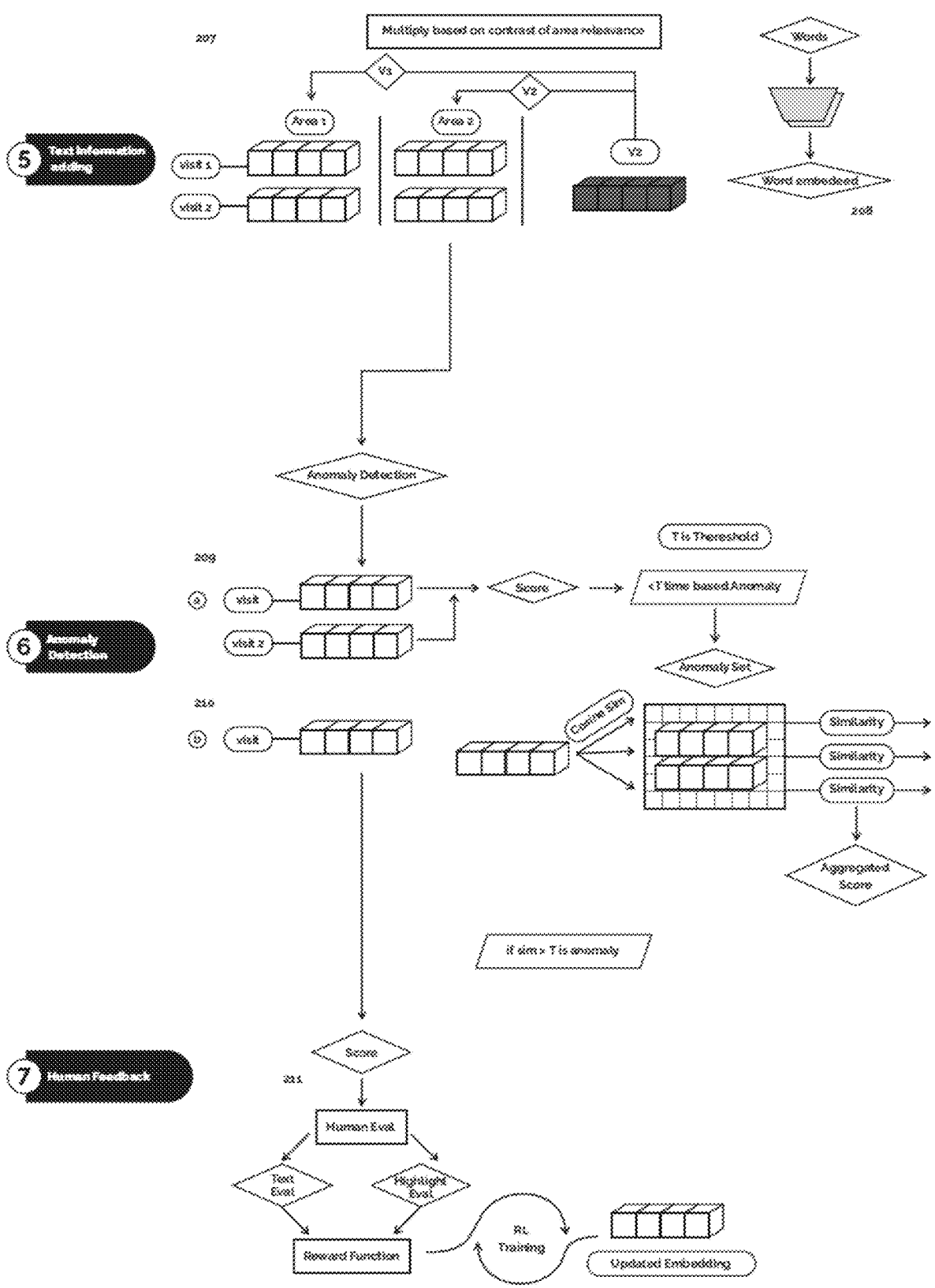
FIG. 3 illustrates three steps in an embodiment of a disclosed method according to aspects of the disclosure.

FIG. 3 illustrates steps in disclosed methods, where the steps include: evaluating text in medical records to identify diagnostically significant language and embedding the identified language with portions of medical images; applying AI to embedded image and textual data to identify anomalies indicative of disease; and human feedback with reinforcement learning to improve the accuracy of the disclosed anomaly detection.

Masking Using Weighted Priors

The masking illustrated in FIG. 2 reduces the overall size and complexity of the data in element 200 to a smaller element 201 required for generating meaningful embeddings. Not all information in medical scans is useful, and due to the challenges posed by high-dimensional data, much of it is redundant or irrelevant. The disclosed methods use masking to selectively identify and weight the most important voxels, ensuring that the most relevant information is retained while reducing unnecessary computation.

The resulting sparse representation of the image allows the disclosed system to efficiently generate embeddings that are both interpretable and computationally manageable. The selection of voxels is based on their significance to specific patient health assessments. Given a dataset of previously identified anomalies, the disclosed methods conduct a probabilistic analysis to determine which anatomical regions are most likely to exhibit pathological changes. For instance, certain areas of the body, such as bones, tissues, and organs, have varying susceptibility to diseases and structural abnormalities. This knowledge is not patient-specific but rather represents a global distribution of health conditions and disease patterns.

By aggregating multiple scans across different individuals, a statistical distribution of ailments emerges, highlighting regions commonly affected by tumors, cancers, fractures, and other medical conditions. Specifically, certain anatomical structures warrant greater attention (e.g., the brainstem, which is susceptible to neurodegenerative diseases and tumors; the lung wall, frequently impacted by fibrosis, cancer, or infections; and the gastrointestinal tract lining, where inflammatory diseases and malignancies often develop). As shown in FIG. 2, element 202, a 3D statistical distribution is thus formed, encoding prior knowledge about where medical abnormalities are most likely to occur. This distribution is generated by combining multiple segmented or highlighted regions across scans, resulting in a spatially-aware probabilistic map that reflects real-world pathological trends.

Mathematically, this concept aligns with prior probability, a fundamental principle in probabilistic machine learning, particularly in Bayesian inference. In the context of healthcare, this is akin to a clinician's intuition-developed through years of experience—about where to focus diagnostic efforts. This intuition effectively guides the disclosed embedding-generation model's attention to the most diagnostically relevant regions.

The masking process functions as a 3D attention mechanism, directing computational resources toward these key areas. This is particularly important for the embedding process since it ensures that the representation captures only the most critical medical features, preventing unnecessary computational overhead and reducing the influence of noise from irrelevant regions. Additionally, the embedding process is sensitive to noise, and including non-informative regions would dilute the quality of the learned representations, making anomaly detection less effective. By leveraging a large corpus of historical medical data, the disclosed methods prioritize regions where anomalies have been observed most frequently, improving both the efficiency and accuracy of disease detection.

The disclosed methods overcome the limitations of prior systems by introducing ailment-aware masking, which enhances the model's attention through the integration of prior knowledge about historically observed anomalies. Unlike conventional approaches that use the entire data representation, the disclosed methods leverage statistical priors derived from previously identified medical anomalies to focus on the most diagnostically relevant regions.

The equations below describe the process of constructing a probability distribution from weighted MRI voxel intensities. Multiple high-quality 3D medical scans are collected, aligned, and preprocessed as described in FIG. 1. Once the voxel-level MRI data is aggregated, an element-wise summation is performed across all aligned images to compute the cumulative intensity at each voxel. To convert these weighted intensities into a probability distribution, we normalize each voxel's intensity by the total sum of all voxel intensities:

$$P(v) = \frac{w(v)}{\sum_{v'} w(v')} \qquad \text{Equation 1}$$

where $w(v)$ represents the voxel intensity at location $v$, and the denominator ensures that the resulting probability density function sums to 1. This transformation guarantees that each voxel's value reflects its relative significance within the entire dataset, allowing the model to incorporate prior knowledge about anatomical regions that frequently exhibit pathological variations.

The probability distribution derived from the aligned 3D medical scans serves as a prior representation, effectively encoding the likelihood of anomalies occurring in different regions of the body. This enables a substantial reduction in search space, filtering terabytes of raw data down to the most diagnostically relevant information.

To further refine the selection process, we introduce a probability threshold $\tau$, which determines the retention of voxel information. Specifically, if the probability of a voxel surpasses $\tau$, its information is retained; otherwise, it is masked out:

$P(v) > \tau$, where each voxel $v$ is defined as $$v = (x_i, y_j, z_k)$$

This thresholding mechanism ensures that only the most significant voxels contribute to the anomaly detection process, eliminating irrelevant or low-probability regions. By selectively preserving high-probability voxels, the model achieves a more efficient and interpretable representation, enhancing both computational efficiency and detection accuracy.

To formalize this process, a disclosed method defines a 3D mask M that encapsulates the selected voxel regions based on the probability threshold. The mask is constructed using the following equation:

$$M_{i,j,k} = \begin{cases} 1, & P(v) > \tau \quad \text{(Include voxel } v_{i,j,k}) \\ 0, & P(v) \le \tau \quad \text{(Exclude voxel } v_{i,j,k}) \end{cases} \qquad \text{Equation 3}$$

This binary mask M effectively retains only the most diagnostically relevant voxels by filtering out regions with a low likelihood of containing anomalies. Once the mask is generated, it is applied element-wise to the original 3D medical scan X, preserving only the selected voxel intensities:

$$X_m = M \odot X \qquad \text{Equation 4}$$

where $\odot$ denotes element-wise multiplication. This operation ensures that all retained voxel intensities remain unchanged while all excluded voxels are set to zero, effectively reducing noise and computational overhead while maintaining critical diagnostic information.

This masking process significantly reduces the region of interest (ROI), minimizing computational overhead by zeroing out irrelevant voxel values. By removing non-essential information, the quality of the embedding is greatly improved, as it retains only the most diagnostically relevant data. This ensures that the next stage of processing focuses solely on meaningful features rather than being diluted by unimportant details. The elimination of low-relevance voxels does not degrade embedding quality, as the neural network captures only the most valuable information in its latent layers. This ailment-specific masking generates high-quality, interpretable embeddings without the burden of unnecessary high-dimensional data, which would otherwise lead to an exponential increase in computation due to spatial correlations in 3D space.

While the primary motivation for masking is to reduce computational complexity-making unsupervised embeddings feasible, the process also enhances embedding quality by eliminating redundant and non-informative voxels. Low-probability voxels, which have minimal influence on anomaly detection, are discarded, ensuring that only the most important features contribute to the final representation. This selective retention of high-impact voxels optimizes both the reconstruction layer of the model and the overall quality of the learned embeddings. Another reason for applying masking is that machine learning models learn to fill in missing portions of the image. This enhances the generalizability of embeddings, as the model must infer missing details from surrounding data points and statistical structures. By conditioning learning on missing regions, the disclosed methods ensure embeddings remain robust and adaptable across different imaging conditions.

The disclosed methods apply masking before anomaly detection by first identifying and extracting regions of interest (ROIs) from 3D medical scans and applying quality enhancements, as shown in FIG. 1. FIG. 1 shows that image quality checks are done before the model processing and anomaly detection. The masking step, done as a data processing step to improve model input, ensures that each anatomical structure or subregion is properly delineated before embeddings are generated, allowing the system to focus anomaly detection on well-defined ROIs rather than entire scans. This prevents unnecessary computational overhead and improves diagnostic accuracy. Each ROI undergoes a transformation, embedding relevant features into a structured vector space, after which the anomaly detection process is customized based on the specific medical condition and organ type. This approach ensures that the disclosed AI system adapts to different anatomical contexts, enhancing precision across diverse medical imaging applications. A practical example of this implementation is as follows: after constructing a prior probability distribution from multiple databases of medical scans, a 3D density map is created as shown in FIG. 2, element 202. This probability map enables targeted refinement by selecting regions based on their likelihood of exhibiting anomalies. For instance, in the case of lung disease detection, the probability map may indicate a higher weighting towards the trachea, where smokers commonly develop issues, compared to the esophagus, which is less frequently affected. Having a baseline probability map prevents the disclosed machine learning model from having to relearn fundamental human anatomy with each training iteration. Instead, it allows the model to prioritize the identification of pathologies in high-risk regions, improving efficiency and accuracy in medical anomaly detection.

Implementation Details:

Medical data may be in 3D scan formats known as DICOM, NIfTI, and MHD (MetaImage). These are standard formats for representing volumetric medical data, including MRI and CT scans. According to aspects of the disclosure, the system is configured to aggregate and store these scan types in a centralized database to create a comprehensive, population-scale statistical representation of medical anomalies. During the data loading phase, the system employs a high-performance computing (HPC) cluster to enable parallel access and simultaneous processing of multiple 3D image volumes. Efficient transfer and memory representation are achieved using Apache Arrow for in-memory columnar data storage and Dask or Apache Spark for distributed data processing and task scheduling across compute nodes. To process and align the volumetric data, the system may utilize a Python-based pipeline that incorporates NiBabel, SimpleITK, and NumPy for loading, resampling, and spatially aligning voxel data from various imaging modalities. These aligned volumes are then aggregated by performing voxel-wise summation and averaging to form cumulative anomaly intensity maps. Intermediate large-scale tensor data is stored in HDF5 or Zarr formats to ensure scalable and efficient I/O performance across high performance computing infrastructure.

Anomaly regions from previously labeled datasets are encoded as binary masks or segmentation overlays, and voxel importance is computed using statistical tools such as Pandas and SciPy. This yields a normalized 3D distribution that captures the prior probability of anomaly presence in specific anatomical regions. To accelerate processing, certain stages—such as cumulative matrix operations—may be GPU-accelerated using CuPy or CUDA kernels. The entire workflow is containerized using Docker or Singularity to ensure reproducibility across systems and can be orchestrated on a cluster via Kubernetes, allowing for scalable deployment in both cloud and on-premise clinical research environments. This results in a weighted spatial distribution of anomaly likelihoods that forms the basis for our masking mechanism, enabling ailment-aware, voxel-level prioritization during the embedding phase.

Process Details:

FIG. 1 illustrates the data acquisition and preprocessing pipeline for 3D medical imaging data prior to the application of masking. The workflow begins with the acquisition of medical image data from one or more hardware providers and/or clinical imaging systems. The acquired data is evaluated for completeness; if metadata or imaging sequences are missing, scan settings are adjusted and a rescan is initiated. Once completeness is verified, the image undergoes a preprocessing phase, which includes normalization, denoising, and intensity correction.

Subsequent to preprocessing, a quality assessment module determines whether the scan meets the resolution and contrast thresholds required for diagnostic analysis. If quality is insufficient, AI-based enhancement methods are applied to improve clarity, contrast, and artifact removal. High-quality images are then routed to a verified repository that may include established medical databases such as The Cancer Imaging Archive (TCIA), the Open Access Series of Imaging Studies (OASIS), and the IXI Database. An annotation validation step is optionally performed to confirm alignment with verified diagnostic labels or expert-reviewed segmentations. This validated and standardized dataset forms the basis for downstream probabilistic masking and embedding generation.

FIG. 2 (element 201) depicts the ailment-aware masking procedure guided by a 3D prior probability distribution. In this step, multiple medical image volumes from population datasets are aggregated and spatially aligned to account for anatomical variability. A probabilistic heatmap is computed by summing or averaging voxel-wise segmentations across the dataset, resulting in a statistical distribution that reflects the frequency of pathological findings across anatomical regions.

This prior probability map is then applied to a new patient scan to generate a binary or weighted mask that retains only the most diagnostically relevant voxels. The masking procedure ensures that regions with a higher likelihood of representing anomalies (such as the brainstem, lung wall, or gastrointestinal tract) are emphasized, while voxels corresponding to less informative areas are suppressed. This process is not merely a compression technique but acts as a spatial attention mechanism that guides the encoder to focus on medically salient regions.

By using ailment-aware masking as a preprocessing step to the embedding pipeline, the system improves the quality of learned representations, reduces unnecessary computational complexity, and enhances the sensitivity of downstream anomaly detection methods. The probability-weighted masking ensures that only regions with high clinical relevance influence the embedding space, leading to more accurate and interpretable diagnostic insights.

Encoding 3D Data to Embeddings

The goal of this section is to describe the embedding generation process, which is applied to the masked voxels obtained from the previous step according to aspects of the disclosure. Traditionally, embedding techniques are widely used in text classification and retrieval-augmented generation (RAG) models, where embeddings are stored in databases to facilitate efficient text search and retrieval. The disclosed methods extend this concept to 3D voxel data, enabling a structured transformation of medical images into a lower-dimensional representation suitable for anomaly detection.

In natural language processing, bidirectional encoder representations from transformers (BERT) is a widely used encoder model that converts words or sentences into high-dimensional embeddings that capture semantic relationships. These embeddings enable downstream tasks such as classification, clustering, and search. BERT learns contextual relationships in text by applying self-attention mechanisms, making it highly effective in capturing meaning from language. Retrieval-augmented generation (RAG) builds on this by incorporating an embedding database where information can be retrieved dynamically during a large language model (LLM) query. In a RAG system, input queries are transformed into embeddings and compared against stored embedding representations, allowing the model to retrieve relevant contextual data. This approach significantly enhances search-based tasks, providing accurate and contextually rich outputs.

The disclosed methods apply a similar concept of embedding generation but in the domain of 3D voxel-based medical imaging. Instead of using BERT to encode text, our method leverages vision transformers (ViT), which apply transformer architectures to image data. ViTs segment an image into patches and process them similarly to how BERT processes tokenized words, using self-attention to learn spatial relationships and features. In addition to this process, we apply custom loss functions during the encoder training to emphasize some of the most important features, which are edges.

Conceptually, ViT can be represented by a learnable weight matrix, $W_{enc}$, which we use to process the masked 3D image $X_m$ and transform it into a compact, lower-dimensional embedding:

$$E = \sigma(W_{enc}X_m + b_{enc}) \qquad \text{Equation 5}$$

where $\sigma$ represents the nonlinear activation functions commonly applied in neural networks. This embedding step ensures that only the most critical structural and statistical information is retained, reducing the dimensionality while preserving meaningful features. The ViT-based encoder enables learning robust representations of medical images, capturing fine-grained structural details and texture variations.

For medical anomaly detection, it is important to retain high-contrast structural details, particularly along anatomical edges. Therefore, an additional edge-aware bias, $b_{edge}$, is introduced into the encoding process. This bias is computed using a 3D Sobel operator, which highlights gradient changes in the image, emphasizing regions that may correspond to medical abnormalities such as tumors or fractures:

$$b_{edge} = \alpha \cdot \text{Sobel}(X) \qquad \text{Equation 6}$$

where $\alpha$ is a scaling factor. Incorporating this bias ensures that the model maintains attention on high-gradient regions that are crucial for detecting structural anomalies.

To reconstruct the original data, the embedding E is passed through a decoder network, represented by the weight matrix $W_{dec}$, which upscales the compressed representation back into the original image space:

$$\hat{X} = \sigma(W_{dec}E + b_{dec}) \qquad \text{Equation 7}$$

In between every matrix multiplication, nonlinearity functions $\sigma$ are applied to enhance feature extraction capabilities.

The training process is guided by a loss function, L, to ensure the embeddings retain the underlying statistical distribution of the original data. This loss function combines multiple objectives:

Kullback-Leibler (KL) Divergence: Commonly used in variational encoders, it ensures that the learned representation maintains a probabilistic similarity to the original data distribution.

Edge Preservation Loss: Ensures that edge features critical to anomaly detection remain intact in the reconstruction.

Reconstruction Loss: Minimizes the difference between the original and reconstructed images.

$$\mathcal{L} = D_{KL}(P_{original}\|P_{encoded}) + \qquad \text{Equation 8}$$
$$\lambda_{edge}\|\text{Sobel}(X) - \text{Sobel}(X)\|^2 + \|X - X\|^2$$

where $\lambda_{edge}$ controls the contribution of edge fidelity to the overall loss function.

This embedding framework ensures that the disclosed model effectively captures essential information from 3D medical images while reducing unnecessary computation. By extending the principles of BERT and RAG embeddings to ViT-based 3D voxel processing with specific focus to medical based masking and biases towards edge reconstruction loss, we enable efficient and precise anomaly detection from the 3d scans. The combination of probability masking, and edge-aware encoding ensures that the embeddings focus on diagnostically relevant regions, improving accuracy in medical imaging applications.

The encoder efficiently processes each scan by integrating previously masked scans as inputs. This integration improves the accuracy of feature extraction by guiding the model's attention toward regions likely to contain abnormalities, lesions, or structural deviations. The pipeline utilizes 3D probability maps that capture latent information about common ailments associated with specific anatomical regions. These maps provide contextual medical knowledge that refines the encoding process, enhancing both computational efficiency and diagnostic precision. The disclosed masking method significantly reduces the volume of voxel data to be processed by focusing on regions of interest identified through the probability map. As shown in FIG. 2, element 203, during training, the masked scan is decoded back into the original 3D scan, preserving spatial relationships and anatomical fidelity. The training loss emphasizes the reconstruction of anatomical edges, which are important for identifying medical conditions. Notably, once the encoder and decoder have been trained for image reconstruction, only the encoder is needed for creating the embeddings.

According to aspects of the disclosure, the encoder serves as the machine learning method responsible for transforming high-dimensional 3D medical scans into structured, lower-dimensional embeddings that retain critical diagnostic information. This encoding step is depicted in FIG. 2 (element 204). An important contribution of the disclosed encoder lies in its ability to generate compact, informative embeddings from 3D images, which can then be used for downstream anomaly detection tasks. These embeddings provide a contextual representation of each scan, enabling the model to identify deviations over time or in comparison with known pathological patterns. Traditional machine learning methods have struggled with the computational demands of processing large voxel-based datasets. In contrast, the disclosed encoder prioritizes diagnostically relevant regions, reducing unnecessary computation and significantly improving the precision and efficiency of feature extraction for medical applications.

In addition to voxel-based embeddings, textual embeddings are also generated using a transformer-based encoder as illustrated in FIG. 3 (element 208). The incorporation of textual documentation alongside masked-based embeddings allows for the correlation of 3D scans with medical reports, enabling a more robust unsupervised learning process. Unlike supervised learning approaches that rely on labeled datasets, this method leverages textual records to provide additional context to the extracted embeddings. Since medical records often contain descriptions of conditions present in scans, textual embeddings serve as complementary information that improves the model's ability to detect anomalies. The textual embeddings differ from the vision-based transformer (ViT) used for 3D voxel processing. Instead, the textual encoder follows a transformer architecture optimized for processing sequential text data, similar to large language models (LLMs). The textual encoding transformation is mathematically expressed as:

$$E_{text} = f_{text}(X_{text}) \qquad \text{Equation 9}$$

where $f_{text}$ is the function that maps textual descriptions into a structured embedding space. The final multimodal representation is obtained by combining both image-based and text-based embeddings using learnable weights $w_{img}$ and $w_{text}$, ensuring that each modality contributes proportionally to the final feature extraction process:

$$E = w_{img}E_{img} + w_{text}E_{text} \qquad \text{Equation 10}$$

This fusion of image and textual embeddings enhances the accuracy of medical anomaly detection by integrating multiple sources of information. By leveraging both structured medical imaging data and unstructured textual descriptions, the system can improve clinical decision-making while maintaining computational efficiency.

Implementation Details:

The masking is applied using the previously described high-performance computing methods, including Dask for parallelized masking operations and Apache Arrow for efficient in-memory voxel data manipulation. The disclosed methods then perform the vision transformer-based embedding generation using libraries such as PyTorch, Hugging Face Transformers, and Monai (Medical Open Network for AI), which provide robust support for 3D medical image models. The model is trained and executed on GPU-accelerated compute environments, including NVIDIA A100 or V100 GPUs, which support mixed precision training for faster convergence. The transformation to embeddings is computationally intensive and is thus performed on an HPC cluster equipped with distributed training orchestration tools like Horovod or PyTorch DDP (Distributed Data Parallel). Signal processing libraries such as SciPy, TorchIO, and SimpleITK are integrated to compute the edge-aware loss components, including 3D Sobel gradients and intensity-based metrics, ensuring accurate emphasis on high-contrast regions during training.

The machine learning framework relies on PyTorch Lightning to manage training logic and optimize hyperparameters, while enabling modular experiment tracking. These custom embeddings are stored in a vector database optimized for similarity search, such as Pinecone, Weaviate, or FAISS (Facebook AI Similarity Search). These systems support rapid retrieval of embeddings during inference and facilitate integration into downstream diagnostic processing and analysis. Although the unsupervised training of the encoder-decoder model is computationally expensive, it is a one-time cost. Once trained, the encoder can be deployed independently for efficient and scalable inference across new 3D scan inputs. The training pipeline ensures that critical diagnostic features are captured in a compact embedding space, combining both medical priors from the probability mask and fine-grained edge sensitivity driven by the custom loss function.

Process Details:

The disclosed embedding generation methods have not previously been applied to 3D voxel-based medical imaging. The proposed approach encodes high-dimensional volumetric features into compact, lower-dimensional embedding vectors, as shown in FIG. 2, element 204. These embeddings are derived from masked 3D image inputs and use dimensionality reduction techniques based on transformer architectures. By integrating 3D Sobel edge detection and masked voxel maps, the disclosed encoder is able to extract detailed structural characteristics such as size, shape variation, and textural patterns—features that traditional 2D-based methods are unable to capture. The information retained in these latent layers is important for both image reconstruction and medical anomaly detection, ensuring that key diagnostic features are preserved throughout the encoding-decoding process.

FIG. 2, element 203 illustrates the encoder training process. Following the application of the probabilistic masking procedure shown in FIG. 2, element 201, the training pipeline includes both an encoder and decoder. The encoder transforms the masked image into an intermediate embedding representation, and the decoder reconstructs the original scan from this latent vector. In contrast, FIG. 2, element 204 focuses on the inference-time use of only the encoder to produce a lower-dimensional vector suitable for downstream tasks such as classification, retrieval, or anomaly detection.

As demonstrated in FIG. 2, element 205, the system supports multimodal integration by combining embeddings across multiple visits or modalities, such as MRI scans and associated textual reports. This fusion allows for longitudinal analysis of a patient's medical history. Embeddings from different timepoints or scan types in element 206 can be stored individually or combined into a unified representation for personalized diagnostics, with downstream retrieval and similarity search supported through vector database indexing.

FIG. 3, element 208 shows how text information is incorporated into the embedding space to enhance the semantic and contextual relevance of medical features. Text-based embeddings—derived from radiologist notes or structured clinical data—are projected into the same latent space as image-based embeddings. As shown in FIG. 3, element 207, these modalities are fused via a lightweight neural transformation layer that emphasizes relevant anatomical regions based on text cues. Inspired by contrastive approaches such as CLIP, the system allows for joint representation of multimodal features that contribute to more interpretable and robust anomaly detection.

Each element of the final embedding corresponds to a learned latent feature capturing spatial, textural, or semantic information critical to diagnosis. Through the combined use of ailment-aware masking, transformer-based encoding, multimodal fusion, and reinforcement learning, embodiments of the disclosed system produces compact and adaptive embeddings optimized for efficient and clinically relevant medical image analysis.

Adaptive Anomaly Detection Using Vectors

Retrieval-augmented generation (RAG) builds on transformer architectures by incorporating an external embedding database from which relevant information can be retrieved dynamically during inference. In typical RAG systems, input queries are converted into embedding vectors and compared with stored representations to retrieve contextually relevant information. While traditionally used for text-based applications, this framework can be extended and adapted for medical anomaly detection, where the goal is to monitor, track, and identify deviations in patient conditions over time. In addition, rather than requiring an additional machine learning algorithm such as a transformer, the disclosed methods instead use much more efficient analytical calculation on the embeddings.

Using embeddings for anomaly detection enables a powerful unsupervised approach that removes the need for manual labeling or handcrafted features. Instead, rich latent embeddings are generated from both 3D medical images and any associated patient data (e.g., reports, visit history). These embeddings encode complex characteristics, such as tissue texture, shape, density, and spatial relationships across anatomical regions. When stored in a vector database, they provide the foundation for scalable and precise anomaly detection. Two primary methods of embedding-based anomaly detection are proposed: (1) temporal comparison-based anomaly detection, and (2) retrieval-based anomaly detection using similarity measures across a population. In this section, we describe the first method in detail.

The temporal comparison-based method monitors changes in patient embeddings over time. Let $E_t$ denote the embedding of a patient's scan at time step t, and $E_t-1$ the embedding from the prior time step. We define the embedding difference as:

$$\Delta E_t = E_t - E_{t-1}. \qquad \text{Equation 11}$$

This difference vector represents how the internal representation of the patient's medical condition has evolved between two visits. To quantify the extent of change, the magnitude of the difference vector is computed using a norm:

$$D_t = \|\Delta E_t\| = \|E_t - E_{t-1}\|. \qquad \text{Equation 12}$$

Here, $D_t$ provides a scalar value measuring how drastically the embedding has shifted. A small value implies routine or gradual changes (e.g., healing tissue or normal aging), while a large value may signify a rapid progression or emergence of pathology.

To determine whether the change is anomalous, this magnitude is compared to a learned threshold $\tau$. The anomaly detection decision at time t is made as follows:

$$\text{Anomaly}(t) = \begin{cases} 1, & D_t > \tau \quad \text{(Anomaly detected)} \\ 0, & D_t \le \tau \quad \text{(No anomaly)} \end{cases} \qquad \text{Equation 13}$$

The threshold $\tau$ is not fixed but dynamically determined based on the distribution of historical embedding changes. Specifically, it is defined as:

$$\tau = \mu_D + k\sigma_D; \qquad \text{Equation 14}$$

where:

$\mu_D$ is the running mean of recent change magnitudes $D_t$, $\sigma_D$ is the standard deviation of these magnitudes, k is a tunable sensitivity parameter.

This formulation allows the system to adapt to individual patients' baseline variability. A larger k makes the anomaly detection stricter, flagging only drastic changes, whereas a smaller k allows for more sensitive detection.

By quantifying the rate of change in the embedding space, the system can distinguish between normal physiological changes (e.g., due to aging, healing, or treatment response) and irregular patterns indicative of emerging medical concerns. This method enables longitudinal monitoring and early detection of anomalies without requiring manual pixel-level supervision or domain-specific feature engineering. This time-aware anomaly detection framework leverages the temporal dynamics of latent representations to provide a clinically relevant signal. It extends the principles of retrieval-augmented architectures by enabling dynamic, personalized anomaly detection based on historical embedding trajectories.

In addition to temporal anomaly detection, a second approach leverages a database of known anomalous embeddings to evaluate whether a new query embedding exhibits similar pathological characteristics. This method compares a query embedding $E_q$ against a stored set of embeddings $\{E_i\}^N_{i=1}$, where each $E_i$ represents a known anomalous condition, such as a past scan with verified structural or pathological abnormalities. This approach can be considered semi-supervised in nature. While it does not require full labeling of all data as normal or abnormal, it does rely on a curated subset of embeddings known to represent anomalous states. The embeddings themselves are still generated using unsupervised methods, preserving generalizability and avoiding overfitting to labeled examples.

The similarity between the query embedding and each stored embedding is calculated using cosine similarity, a standard metric for comparing vector directions regardless of magnitude:

$$S(E_q, E_i) = \frac{E_q \cdot E_i}{\|E_q\|\|E_i\|}. \qquad \text{Equation 15}$$

Here, $E_q \cdot E_i$ is the dot product of the query and reference embeddings, and $\|E_q\|$ and $\|E_i\|$ denote their respective Euclidean norms. Cosine similarity ranges from $-1$ to $1$, where 1 indicates identical orientation (high similarity), and lower values indicate divergence.

To assess the overall similarity of the query embedding to the anomalous class, we compute the mean similarity score across all stored embeddings:

$$S_{overall} = \frac{1}{N}\sum_{i=1}^{N} S(E_q, E_i). \qquad \text{Equation 16}$$

This averaging step allows the anomaly detection using embeddings to consider the global similarity of the new scan to a distribution of known abnormal cases, rather than relying on a single nearest neighbor as done in traditional retrieval-augmented systems.

An anomaly is then detected when the overall similarity falls below a predefined threshold, indicating that the query embedding significantly diverges from the anomalous reference class:

$$\text{nomaly}(E_q) = \begin{cases} 1, & S_{overall} < \tau_s \quad \text{(Anomaly detected)} \\ 0, & S_{overall} \ge \tau_s \quad \text{(No anomaly)} \end{cases} \qquad \text{Equation 17}$$

The threshold Ts can be tuned based on validation data or statistical confidence intervals. Unlike classification models, this method allows for flexible decision boundaries based on similarity distribution, making it more robust in clinical settings where anomalies may span a wide spectrum of manifestations. This method is especially effective for handling rare or edge-case conditions, where labeled data is scarce, but examples of anomalies exist in previously encountered patients. Additionally, it allows for continual updating of the anomaly database—new embeddings can be added without retraining the previously mentioned embedding-generation model, enabling rapid adaptation to new medical scenarios. Because this method uses a single similarity aggregation step rather than retrieving and passing contextual data into a second-stage generative model (as in traditional RAG pipelines), it is significantly faster and more lightweight in terms of memory. This efficiency makes it well-suited for real-time diagnostic pipelines, large-scale screening applications, and longitudinal health monitoring frameworks where response time and scalability are critical. Implementation Details:

The computations required for this anomaly detection framework—such as thresholding, vector subtraction, cosine similarity, and norm calculations—are lightweight and well-suited for analytical execution without additional deep learning inference. These operations can be efficiently distributed across a networked RAG (Retrieval-Augmented Generation) infrastructure, enabling parallel execution of similarity comparisons and threshold evaluations across geographically dispersed systems. To support real-world scalability, the vector database can be deployed using distributed and fault-tolerant systems such as Pinecone, Weaviate, or FAISS. These systems allow the data to be split across multiple machines and enable parallel searching, making it faster and more reliable even as the amount of data grows. These databases may run on nodes equipped with NVMe-based SSDs for high-throughput, low-latency access to embedding vectors. Deployment over edge computing environments is enabled via container orchestration platforms like Kubernetes and Docker Swarm, where each node hosts a subset of the global vector database alongside local patient embeddings.

In a typical setup, the initial embedding generation for a patient scan is performed at a local site, such as a medical assistant workstation or radiology room, using a compact GPU unit such as NVIDIA Jetson AGX Orin, RTX A4000, or edge-grade A100 Tensor Core GPU, depending on performance requirements. Once generated, the embedding vector is transmitted to a centralized inference hub or regional datacenter, where large-scale vector similarity search is performed. This transmission is handled via high-bandwidth, low-latency networking infrastructure such as InfiniBand, RDMA over Converged Ethernet (ROCE), or 100/200 Gbps Ethernet, allowing for fast movement of embeddings between compute nodes. The embeddings may be serialized using formats such as FlatBuffers or Protocol Buffers to reduce overhead during transfer.

Training of the initial embedding model and threshold adaptation mechanisms is performed on a GPU-accelerated high-performance computing cluster, utilizing NVIDIA DGX systems or cloud-based GPU instances (e.g., AWS p4d, Azure NDv5). These systems support distributed training protocols such as NCCL (NVIDIA Collective Communications Library) and Horovod, which enable parallel optimization of the encoder across multiple GPUs and nodes. The advantage of this setup is that local nodes handle inference and embedding generation with minimal latency and resource overhead, while global systems perform population-wide comparisons and anomaly detection in near-real-time. This federated computing model also supports privacy-preserving architectures, allowing only the minimal required data (i.e., latent vectors, not full scans) to be transmitted between nodes, in compliance with data privacy regulations such as HIPAA and GDPR. By distributing both computation and storage, and by leveraging efficient communication backbones and vector-aware databases, embodiments of the disclosed system achieve real-time anomaly detection, low deployment overhead, and robust scalability across medical facilities and healthcare networks.

Process Details:

In FIG. 1, the decision point for anomaly detection is illustrated, occurring after the initial masking and segmentation steps but prior to the radiologist's review and human feedback integration. Anomaly detection serves as a critical gating mechanism to determine whether downstream model refinement or report finalization should proceed.

FIG. 3, element 209 depicts the first anomaly detection method, in which embeddings from multiple patient visits over time are compared. This time-based anomaly detection approach identifies significant deviations between consecutive visit embeddings, allowing for longitudinal tracking of potential disease progression.

FIG. 3, element 210 illustrates the second method, wherein a current embedding vector is compared to a database of previously identified anomalies using a similarity metric such as cosine similarity. This method supports semi-supervised anomaly detection by identifying latent space proximity to known pathological patterns.

Each of these methods employs a distinct thresholding mechanism to determine whether an embedding represents an anomalous case. In the time-based approach, the threshold is computed based on historical variation within a single patient's embedding trajectory. In the similarity-based method, the threshold reflects the distribution of similarity scores to the reference anomaly set.

Embedding Updates Through Human Feedback

The disclosed methods integrate reinforcement learning (RL) to iteratively refine embeddings over time using human-in-the-loop feedback. This approach is particularly applicable in the medical domain, where expert validation may be required. For instance, in transformer-based architectures such as large language models (LLMs), user feedback—like thumbs-up or thumbs-down inputs—drives reward mechanisms that adjust specific model weights. The disclosed methods build upon this principle with a more structured and domain-specific feedback loop.

In the disclosed system, human-provided corrections—such as revised textual inputs or highlighted anomalous regions in imaging data—are treated as reinforcement signals. These inputs guide the adjustment of embedding weights to improve the accuracy and interpretability of the representations. When textual feedback is involved, similarity metrics—such as term frequency-inverse document frequency (TF-IDF) or cosine similarity—quantify overlap between system-generated content and expert annotations as segmented highlights. This overlap score is used as a reward signal, reinforcing beneficial adjustments. As a clarification, segmentation is the selection of an area in the 3d scan to reinforce a certain generation area, whereas masking is the nulling out of information during the training process.

Compared to retraining embeddings from scratch every time new data or feedback is introduced, reinforcement learning (RL) provides a more efficient and adaptive mechanism. Starting over can be computationally expensive and may discard previously learned useful representations. In contrast, RL allows the system to build upon prior knowledge, fine-tuning embeddings in a targeted manner without disrupting the global structure. This continual refinement ensures faster convergence and preserves generalization across similar diagnostic contexts, especially important in environments with evolving data and limited expert availability.

The disclosed framework also supports multimodal embeddings by integrating textual documentation with imaging data. These are fused through a weighted formulation, combining textual embeddings (from clinical notes or structured medical records) with imaging-based embeddings (from modalities such as X-rays or MRIs). This multimodal fusion is jointly optimized through reinforcement learning, where feedback may span across both modalities. For example, an expert might annotate a specific region in an image while providing related clinical notes—both contributing to the reward signal. Together, these components form a diagnostic framework that continuously improves with both data-driven signals and human expertise, enabling adaptive, interpretable, and high-performance medical decision support.

According to aspects of the disclosure, reinforcement learning plays a central role in dynamically updating the embedding by incorporating human feedback. The feedback-based update model refines its learned embeddings over time through an update rule of the form $$E_{t+1} = E_i + \eta \nabla R_t, \qquad \text{Equation 18}$$

Where $E_t$ represents the current embedding, $\eta$ is the learning rate, and $\nabla R_t$ is the gradient of the expected reward. This formulation enables the system to make iterative improvements based on sparse, targeted feedback, rather than restarting training from scratch—making it significantly more efficient and responsive in dynamic domains like healthcare.

The expected reward at time step t, denoted by $$R_t = \mathbb{E}[r_t | \pi(E_t)], \qquad \text{Equation 19}$$

models the anticipated feedback from human experts, given the current policy or embedding $\pi(E_t)$. The gradient of this reward, used for updating the embeddings, follows $$\nabla R_t = \mathbb{E}[r_t \nabla \log \pi(E_t)], \qquad \text{Equation 20}$$

which is a standard form from policy gradient methods, where $r_t$ reflects the feedback signal provided by the expert.

In the textual modality, rewards are computed based on the similarity between expert-provided descriptions and the system-generated text. Specifically, TF-IDF-based cosine similarity is used to measure semantic overlap between the corrected and predicted text. Higher similarity implies a more accurate embedding, thus yielding a higher reward. This textual reward mechanism encourages the embeddings to align with human interpretation and diagnostic language. Because TF-IDF captures the importance of domain-specific terms (e.g., "spiculated," "hyperdense," "non-calcified"), it ensures that embeddings become more sensitive to medically relevant language patterns over time.

In parallel, segmentation-based rewards are structured around spatial feedback. The model's segmentation predictions are defined as $$S_t = f_\theta(X), \qquad \text{Equation 21}$$

where X is the input image and $f_\theta$ is the model's current parameterization. When an expert provides a corrected segmentation mask $H_t$, the reward is computed as $$R_t = \sum_{v \in H_t} \delta(S_t(v), H_t(v)), \qquad \text{Equation 22}$$

where $\delta(S_t(v), H_t(v))$ is a similarity function measuring overlap between the predicted and annotated segmentation for each pixel or voxel v. In practice, this function may be implemented as the Dice coefficient, Intersection over Union (IoU), or a binary similarity score—all of which provide dense, localized supervision.

By using these reward functions—TF-IDF similarity for textual feedback and pixel-wise overlap for segmentation corrections—the feedback-based update model is able to accurately pinpoint discrepancies between its predictions and human expert guidance. These feedback signals provide meaningful gradients that adjust embeddings not only globally, but also in terms of localized features and semantic context.

Unlike traditional systems that require retraining on fully labeled datasets, this framework allows for real-time, continuous refinement of embeddings. Experts can intervene with segmentation adjustments, textual clarifications, or classification feedback, all of which are immediately translated into reinforcement signals. For example, if a radiologist identifies a false positive lesion, they can annotate it with a descriptive label (e.g., "scan distortion, not a lesion"). This textual input is encoded and compared to the model's output using TF-IDF similarity, contributing to the embedding update in a meaningful way. Such dynamic textual integration allows the system to generalize to previously unseen conditions without the need for extensive manual labeling or re-engineering.

Ultimately, the disclosed approach yields a highly adaptive, expert-aligned diagnostic framework. It improves continuously through direct interaction with medical professionals, incorporating both visual and semantic feedback to refine its internal understanding and output accuracy.

Implementation Details:

The integration of reinforcement learning with human-in-the-loop feedback is implemented using a scalable backend that supports real-time interaction and embedding updates. Human feedback—whether in the form of corrected segmentation masks or textual clarifications—is captured via clinician interfaces deployed on secure, HIPAA-compliant edge devices (e.g., medical workstations or tablets), often hosted on virtual desktop infrastructures (VDIs) within the hospital network. Once collected, this feedback is securely transmitted using TLS-encrypted RESTful APIs or FHIR-based messaging protocols, ensuring interoperability with existing electronic health record (EHR) systems.

The embedding update pipeline runs on a hybrid compute environment consisting of on-premise GPU servers (e.g., NVIDIA A100, RTX 6000 Ada, or JetsonAGX Orin for low-latency edge inference) and cloud-based reinforcement learning infrastructure deployed on platforms such as AWS SageMaker RL, Azure Machine Learning, or Google Vertex AI. The embedding update logic is parallelized using Ray RLlib or TorchRL, and the environment state—including historical feedback, model parameters, and patient-specific embeddings—is versioned using DVC (Data Version Control) or MLflow.

To propagate gradient updates efficiently across distributed RL agents, the system uses parameter servers with gRPC communication and supports NCCL (NVIDIA Collective Communications Library) for fast, multi-GPU interconnect. Feedback batches are queued and prioritized based on clinical relevance using a priority scheduling mechanism implemented with Apache Kafka or RabbitMQ, ensuring time-sensitive expert corrections are processed ahead of bulk update tasks.

For segmentation-based feedback, 3D image rendering libraries such as VTK, ITK, and SimpleITK are used for visualization and annotation, with feedback encoded as binary voxel masks and stored in compressed NRRD or NIfTI formats.

Textual feedback, including descriptive clinical notes, is preprocessed using spaCy, ScispaCy, or BioBERT tokenizers, and vectorized using a combination of TF-IDF, BERT, or Sentence-BERT encoders. Cosine similarity calculations are accelerated with NumPy, Faiss, or cuML, enabling fast similarity lookups in high-dimensional embedding spaces. All embedding modifications are logged, auditable, and reversible via delta-tracking modules stored in immutable storage volumes (e.g., AWS S3 Glacier or Ceph), allowing clinicians to trace model behavior over time.

The disclosed distributed, low-latency system enables continuous fine-tuning of embeddings with human supervision while maintaining high throughput, fault tolerance, and data integrity. It bridges expert feedback with modern machine learning operations infrastructure, making the reinforcement process both interpretable and clinically actionable.

Process Details:

As shown in FIG. 1, the human feedback loop occurs after the initial anomaly detection stage. If a prediction's confidence score—calculated as the difference between the observed embedding and the expected distribution—is close to a decision threshold, a radiologist may be prompted to review the case. Their corrections, provided in the form of textual annotations, segmentation masks, or classification updates, are then used to refine the system's internal representations. Because updates are applied at the embedding level rather than through full model retraining, the system adapts rapidly while minimizing computational overhead.

While the disclosed methods incorporate unsupervised learning components, the ability to incorporate human feedback represents an important enhancement. This human-in-the-loop approach allows iterative modification of embedding vectors based on expert input. As illustrated in FIG. 3, element 211, when a radiologist identifies a false positive or misclassification, they can append a textual correction or modify the segmentation. The updated embedding is selectively retained in the vector database, thereby improving the accuracy of future retrieval and classification tasks. This mechanism of embedding refinement through direct human feedback enhances both contextual accuracy and interpretability.

Furthermore, when embeddings from multiple modalities (e.g., 3D image and textual report) are fused using weighted vector addition, the combined representation retains salient features from each modality. Owing to the properties of cosine similarity, the fused embedding remains sensitive to dominant features contributed by either modality. This design supports robust classification and retrieval even when only one data source is present during inference.

FIG. 3, element 211 also illustrates how segmentation and textual feedback are encoded into updated embeddings through a reinforcement learning mechanism. These updates are applied incrementally to the latent space, enabling continual learning without requiring full reinitialization or retraining of the encoder architecture.

Technical Architecture

The present disclosure relates to a secure, scalable, and compliant technology framework for AI-driven medical data processing. The system implements a hybrid compute environment utilizing CPU, GPU, and TPU resources for accelerated AI operations, orchestrated through auto-scaled Kubernetes clusters and edge computing nodes. Data storage follows a multi-tiered model, separating active datasets, processed datasets, and historical records across hot, warm, and cold storage layers, respectively.

Security is integrated at every layer through homomorphic encryption at ingestion, AES-256 encryption at rest and in transit, Zero Trust Architecture with mandatory multi-factor authentication (MFA), real-time encryption key rotation, and privileged access management via Role-Based and Attribute-Based Access Controls (RBAC and ABAC). To meet regulatory and privacy requirements, the platform enforces full compliance with HIPAA, GDPR, HITRUST, SOC 2, and ISO 27001 standards. Auditability and transparency are achieved through blockchain-backed immutable logs and automated compliance reporting.

Illustrative Use Cases

Use Case 1: Database Comparison for Acute Head Injury A patient arrives at the emergency department following a vehicular accident and undergoes a 3D CT scan. The system encodes the scan into an embedding vector using the described architecture. This embedding is transmitted and compared against a reference database populated with prior embeddings from cases involving post-vehicle collision injuries. The system identifies high-similarity matches and returns example cases and similarity metrics to assist the physician in evaluating the patient's condition.

Use Case 2: Temporal Anomaly Detection for Cardiac Symptoms A patient presenting with chest pain undergoes a thoracic CT scan. A prior scan from an earlier visit is available. The system embeds both scans and calculates a difference between the resulting vectors. If this difference exceeds a predefined threshold, the scan is flagged for review. Patient-specific data such as previous conditions and treatments may influence the sensitivity of the detection. This enables comparison over time to detect potential changes in cardiac structure.

Use Case 3: Outpatient Evaluation for Lower Back Pain A 49-year old male visits an orthopedic clinic with lower back pain after a physical strain. An MRI scan is performed. The system generates an embedding vector from the scan and combines it with structured clinical textual metadata such as injury history and reported symptoms. The embedding is evaluated against stored examples to assess potential abnormalities. Visual outputs, including heatmaps and similarity scores, are presented to the physician. The embedding may be retained for future use in follow-up assessments.

What is claimed:

1. A method for masking 3D medical images, comprising:
   receiving a plurality of 3D medical image volumes formatted in DICOM, NIfTI, or equivalent formats;
   computing a voxel-wise prior probability distribution over anatomical regions by aggregating voxel intensities from the plurality of image volumes;
   generating a spatial mask that selectively retains voxels having prior probability values $P(v)$ greater than a threshold, such voxels representing regions with elevated likelihood of containing pathological features as determined from aggregated historical imaging data; and
   applying the spatial mask to each new 3D image to reduce dimensionality and focus downstream processing on regions associated with pathological abnormalities including tumors, lesions, fractures, or structural deviations.

2. The method of claim 1, wherein computing the voxel-wise prior probability distribution comprises:
   performing an element-wise summation of voxel intensities across a dataset of spatially aligned 3D medical image volumes, followed by normalization of the summed voxel intensities to produce a probability density function whose total voxel intensity values sum to one.

3. The method of claim 1, wherein applying the spatial mask comprises:
   applying the binary mask to each new 3D medical image via element-wise multiplication to preserve voxel intensities in said regions associated with pathological abnormalities.

4. The method of claim 1, wherein the spatial mask is ailment-aware and reflects prior knowledge of anatomical regions affected by specific medical conditions, such that applying the spatial mask to each new 3D image functions as a three-dimensional attention mechanism directing input emphasis toward said regions associated with pathological abnormalities when the masked image is processed by a downstream machine learning model.

5. A method for encoding medical data into a shared latent space, comprising:

encoding a masked 3D medical image prepared according to the method of claim 1 into a first embedding vector using a vision transformer-based encoder;

encoding an associated textual medical report into a second embedding vector using a language model-based encoder;

projecting both the first and second embedding vectors into a shared latent vector space; and storing a resulting multimodal embedding in a vector database for downstream comparison and retrieval.

6. The method of claim 5, wherein the vision transformer-based encoder is trained jointly with a decoder network to reconstruct the 3D medical image from said first embedding vector, wherein training includes masked input images generated by ailment-aware spatial masking, and the decoder is used only during training.

7. The method of claim 5, wherein the encoder is trained using a composite loss function comprising:

a reconstruction loss that minimizes a difference between an original 3D medical image and an image decoded from the first embedding vector;

a Kullback-Leibler divergence term that regularizes a latent space distribution; and an edge-preservation loss that applies a 3D Sobel operator to emphasize regions where voxel intensity exhibits gradient changes as measured using a 3D Sobel edge detection operator.

8. The method of claim 5, further comprising projecting the textual embedding and the 3D image embedding into a common latent space using modality-specific projection weights, and combining the projected textual embedding and the projected 3D image using a weighted summation to produce a final multimodal embedding vector.

9. The method of claim 5, comprising:

a. receiving human-annotated segmentation masks indicating corrected regions of interest in a 3D medical image;

b. receiving textual corrections to associated medical reports, the corrections comprising diagnostic descriptions;

c. computing reward signals based on overlap between predicted segmentations and corrected masks, and based on semantic similarity between original and corrected textual descriptions;

d. updating encoder parameters or embedding vector representations based on computed reward signals using a reinforcement learning update rule; and repeating steps a-d to incrementally refine a latent representation space over time with continued expert interaction.

10. The method of claim 9, wherein the reward signal for textual feedback is computed using term frequency-inverse document frequency (TF-IDF) weighted cosine similarity between system-generated descriptions and human-provided corrected descriptions, such that a higher similarity corresponds to a higher reward.

11. The method of claim 9, wherein the reward signal for image-based feedback is computed by measuring spatial overlap between a predicted segmentation mask and a human-annotated segmentation mask using a similarity function selected from a group consisting of Dice coefficient, Intersection over Union, and binary overlap.

12. The method of claim 9, wherein the multimodal embedding is updated using a reinforcement learning update rule that adjusts the multimodal embedding via a gradient ascent step on an expected reward, and wherein the reward signal is computed as a weighted combination of textual similarity and segmentation overlap based on human-provided feedback, such that both clinical descriptions and image annotations contribute to the embedding refinement.

* * * * *